US00PP27060P3

(12) United States Plant Patent
Costa et al.

(10) Patent No.: US PP27,060 P3
(45) Date of Patent: Aug. 16, 2016

(54) ***ACTINIDIA CHINENSIS* PLANCHON PLANT NAMED 'AC1536'**

(50) Latin Name: *Actinidia chinensis Planchon*
Varietal Denomination: AC1536

(71) Applicants: ALMA MATER STUDIORUM—UNIVERSITA' DI BOLOGNA, Bologna (IT); UNIVERSITA' DEGLI STUDI DI UDINE, Udine (IT)

(72) Inventors: Guglielmo Costa, Bologna (IT); Raffaele Testolin, Udine (IT); Guido Cipriani, Udine (IT)

(73) Assignees: ALMA MATER STUDIORUM—UNIVERSITA' DI BOLOGNA, Bologna (IT); UNIVERSITA' DEGLI STUDI DI UDINE, Udine (IT)

( * ) Notice: Subject to any disclaimer, the term of this patent is extended or adjusted under 35 U.S.C. 154(b) by 240 days.

(21) Appl. No.: 13/987,767

(22) Filed: Aug. 29, 2013

(65) Prior Publication Data

US 2014/0082777 P1 Mar. 20, 2014

(30) Foreign Application Priority Data

Aug. 29, 2012 (QZ) ..... 20121668

(51) Int. Cl.
*A01H 5/08* (2006.01)

(52) U.S. Cl.
USPC ..... Plt./156
CPC ..... *A01H 5/08* (2013.01)

(58) Field of Classification Search
USPC ..... Plt./156
CPC ..... A01H 5/08
See application file for complete search history.

*Primary Examiner* — Kent L Bell
(74) *Attorney, Agent, or Firm* — Marshall, Gerstein & Borun LLP

(57) ABSTRACT

A new and distinct *Actinidia chinensis Planchon* cultivar named AC1536 is disclosed, characterized by distinctive large, oblong fruit, and an earlier time of maturity for harvesting.

8 Drawing Sheets

Latin name of the genus and species: *Actinidia chinensis Planchon.*

Variety denomination: 'AC1536'.

BACKGROUND OF THE INVENTION

The new cultivar is a product of a planned breeding program in Italy under the direction of the Guglielmo COSTA, Raffaele TESTOLIN, and Guido CIPRIANI, all Italian citizens. The seed parent is the seedling variety referred to as *Actinidia chinensis Planchon* A0172. The pollen parent is the seedling variety referred to as *Actinidia chinensis Planchon* 'A0134.16'.

Fruit of the new variety was first evaluated in year 2003 with favorable results. After the first evaluation, semi-hardwood cuttings were made of 'AC1536' and were grafted onto Hayward, *Actinidia deliciosa*, as rootstocks. Evaluation, asexual propagation, and grafting all first took place at the inventor's commercial nursery in Bologna, Italy. Subsequent evaluations of the variety have shown the characteristics to be true to type.

SUMMARY OF THE INVENTION

The cultivar 'AC1536' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'AC1536'.

These characteristics in combination distinguish 'AC1536' as a new and distinct *Actinidia chinensis Planchon* cultivar:

1. Distinctive size and shape of fruit.
2. Early time of maturity for harvesting.

COMPARISON TO PARENT

Plants of the new cultivar 'AC1536' are similar to plants of the seed parent, *Actinidia chinensis Planchon* 'A0172' in most horticultural characteristics. However, plants of the new cultivar 'AC1536' produce fruit several weeks earlier than Hayward and Hort16A. Average fruit weight of 'AC1536' is 105 grams compared to other *A. chinensis* cultivars which average fruit weight ranged from 75 to 100 g.

Plants of the new cultivar 'AC1536' are similar to plants of the pollen parent, *Actinidia chinensis* 'A0134.16' in some horticultural characteristics. However, as the sex expression of 'A0134.16' is male, plants of 'A0134.16' produce only male flowers, whereas the sex expression of 'AC1536' is female, and plants produce female flowers that in turn develop into large fruit.

COMMERCIAL COMPARISON

The new variety is best compared to the commercial varieties Soreli, Hort16A (U.S. Plant Pat. No. 11,066), and Jintao. AC1536 is similar to Soreli in many horticultural characteristics, but 'AC1536' bears oblong fruit, and bears the fruit earlier in the season than Soreli.

'AC1536' is similar to Hort16A in many horticultural characteristics, but 'AC1536' bears fruit that does not have the protruding beak found in fruit of Hort16A. Moreover, fruits of 'AC1536' ripen earlier in the season and the flowering takes place later in the season with respect to Hort16A.

'AC1536' is similar to Jintao in many horticultural characteristics, but 'AC1536' bears larger fruit than Jintao, and bears the fruit earlier in the season. Fruits of 'AC1536' are less prone to develop cracks.

BRIEF DESCRIPTION OF THE PHOTOGRAPH

The accompanying photographs in FIGS. 1 and 2 illustrate in full color typical buds on plants of 'AC1536'.

Figure 1:
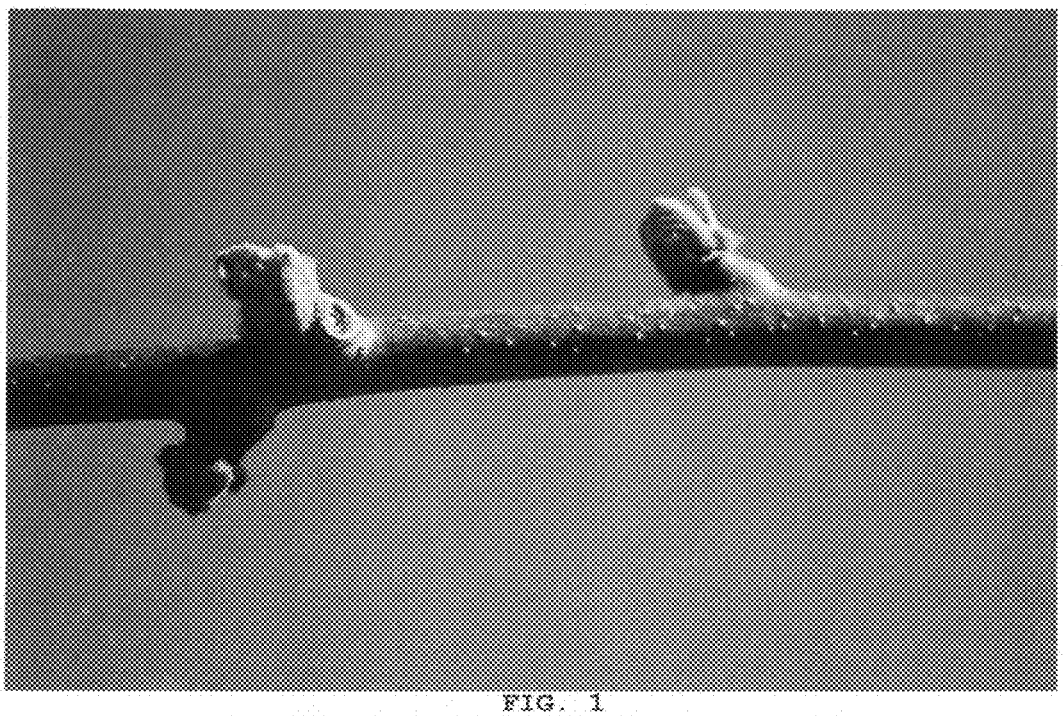
Figure 2:
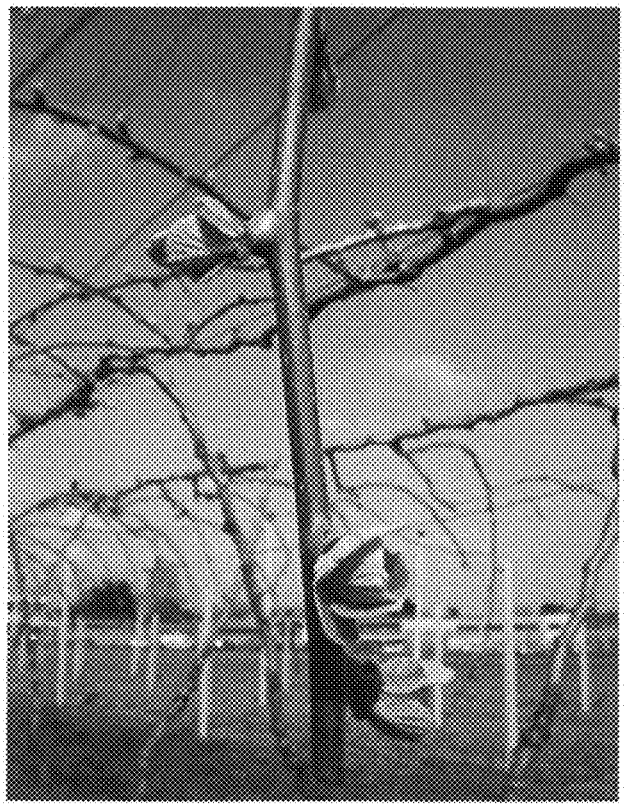
Figure 3:
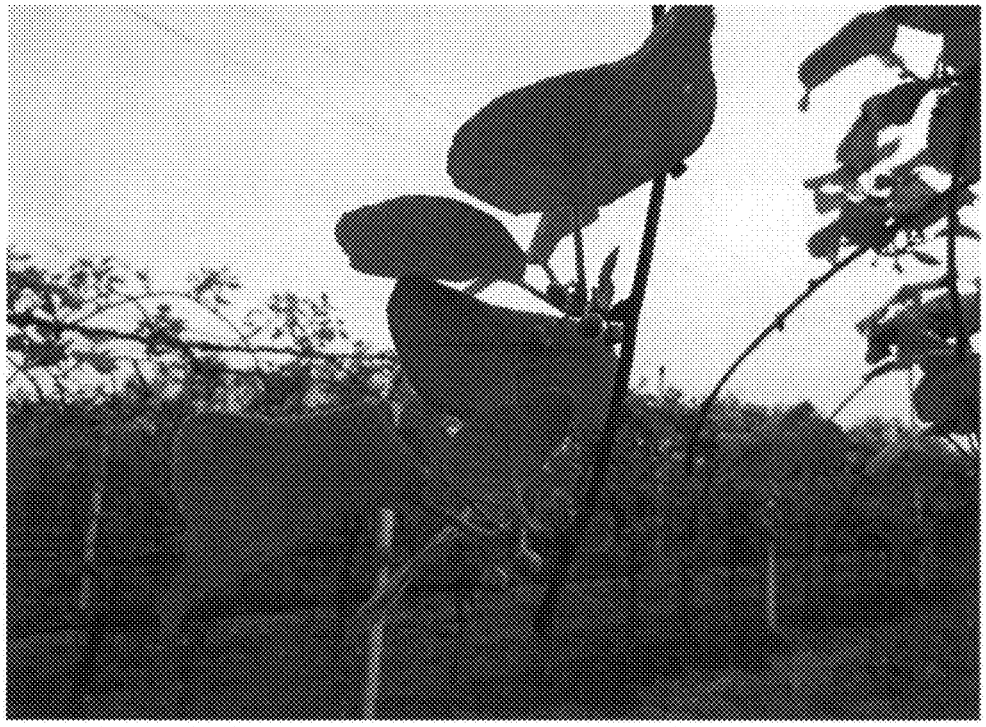
FIG. 3 illustrates in full color typical foliage of 'AC1536'.
Figure 4:
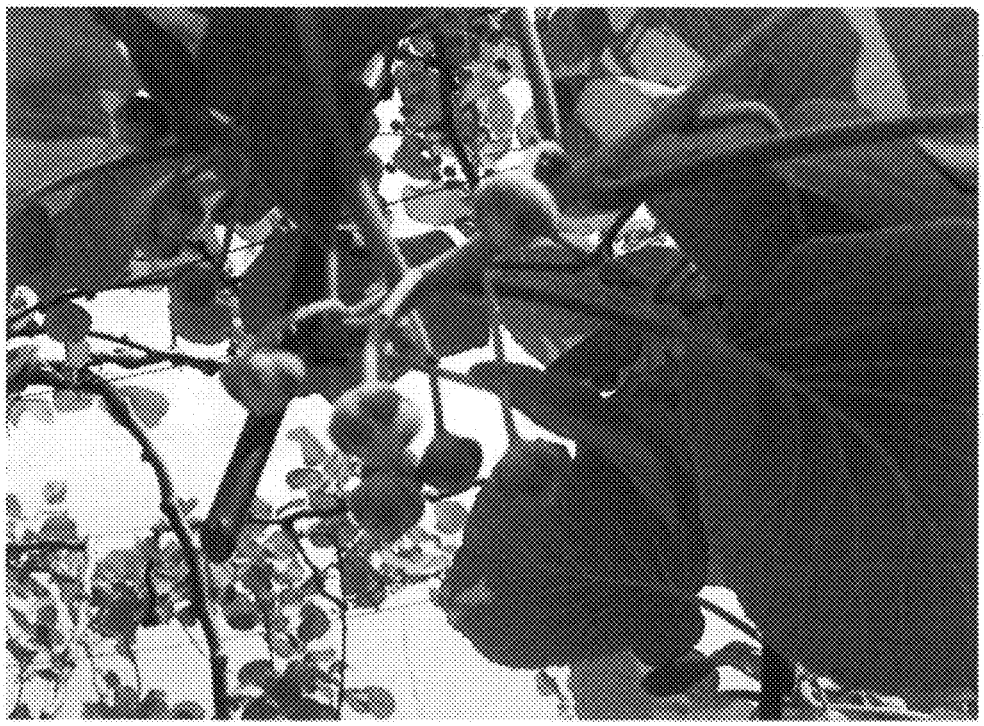
FIGS. 4-8 illustrate in full color typical flowers of 'AC1536'.
Figure 5:
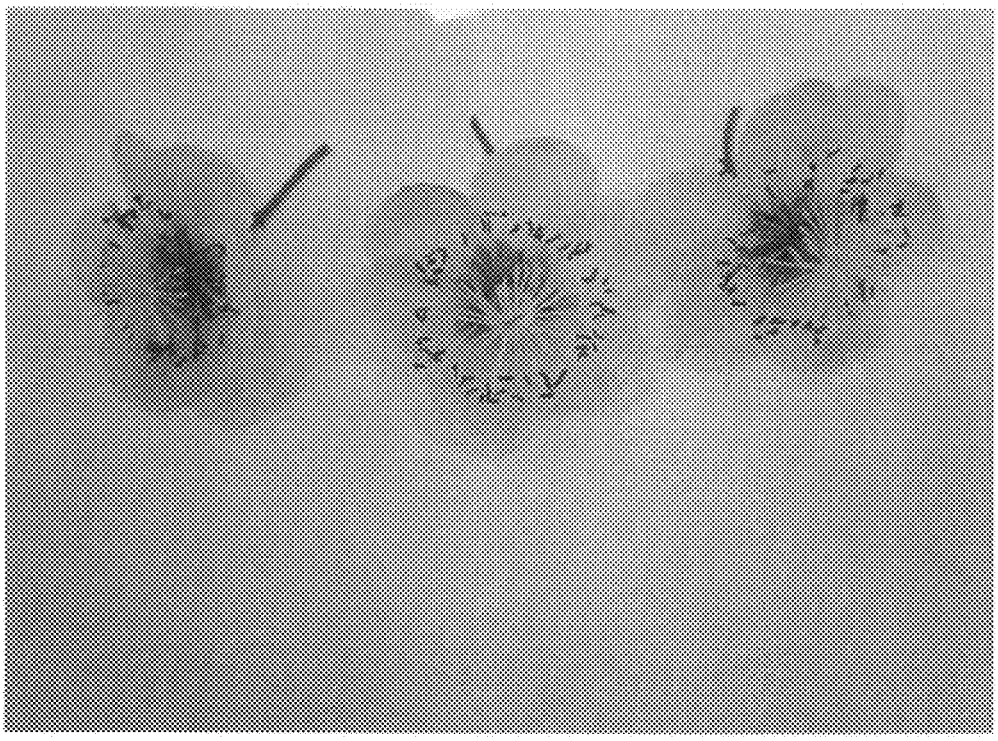
Figure 6:
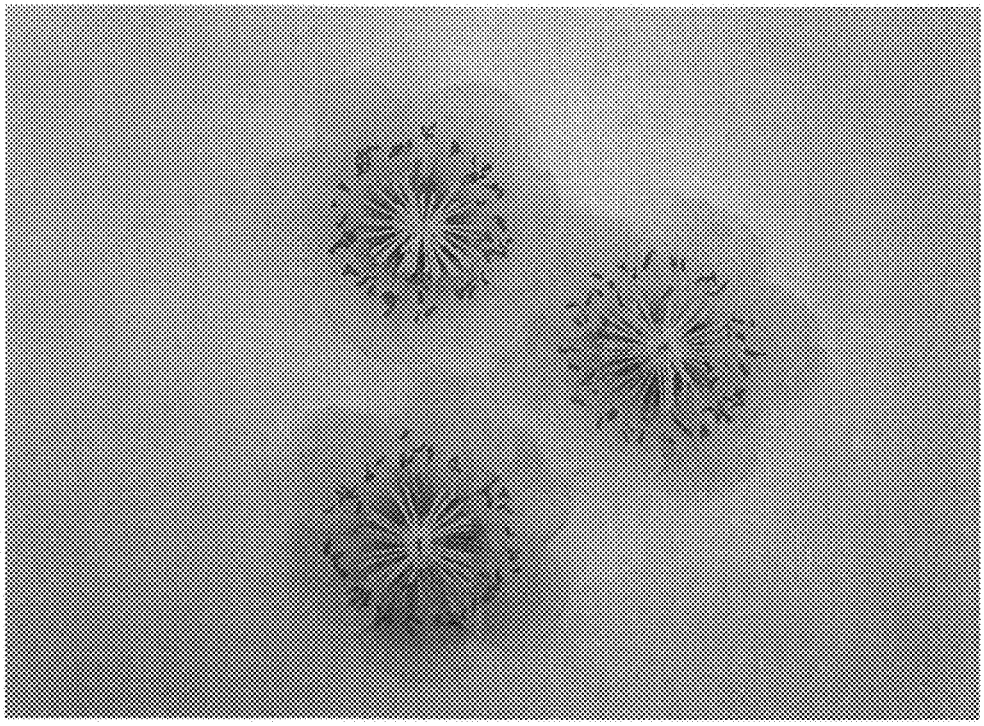
Figure 7:
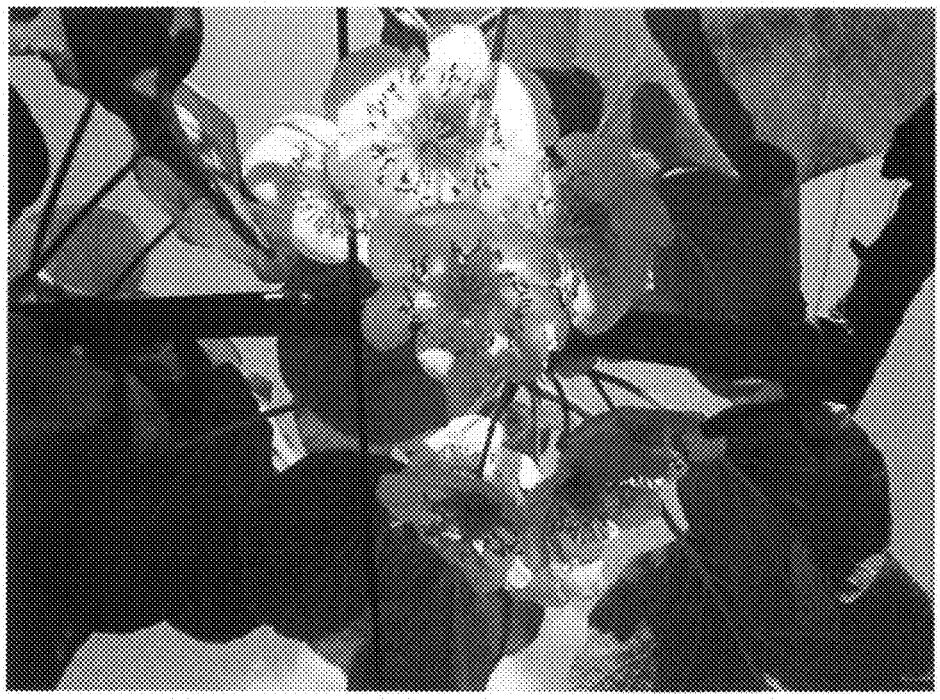
Figure 8:
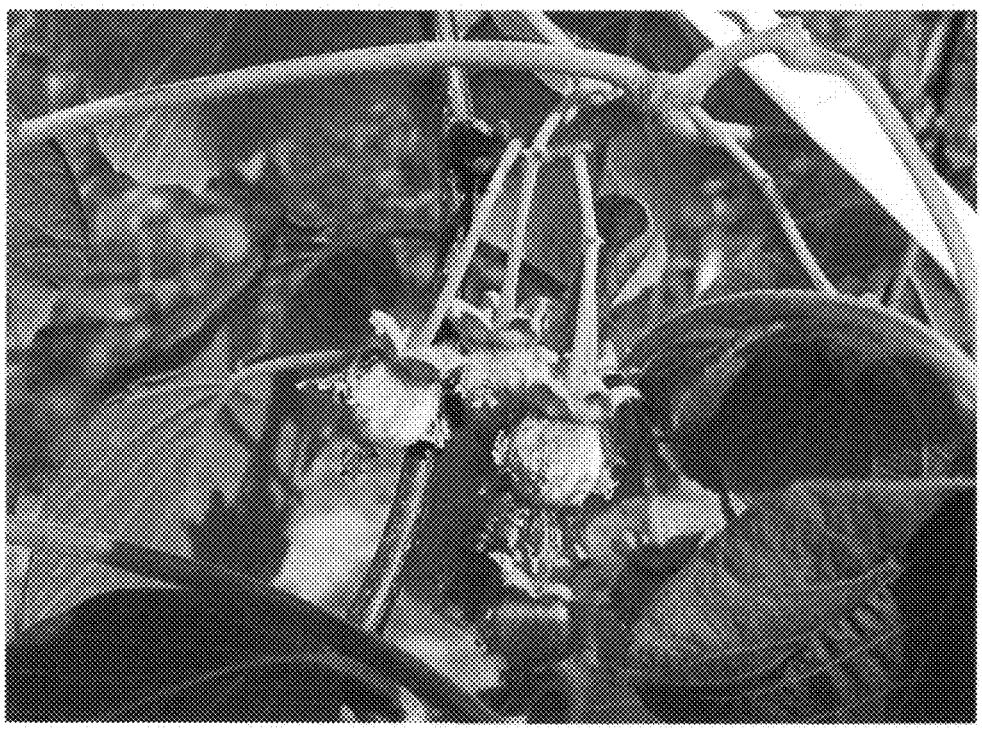
Figure 9:
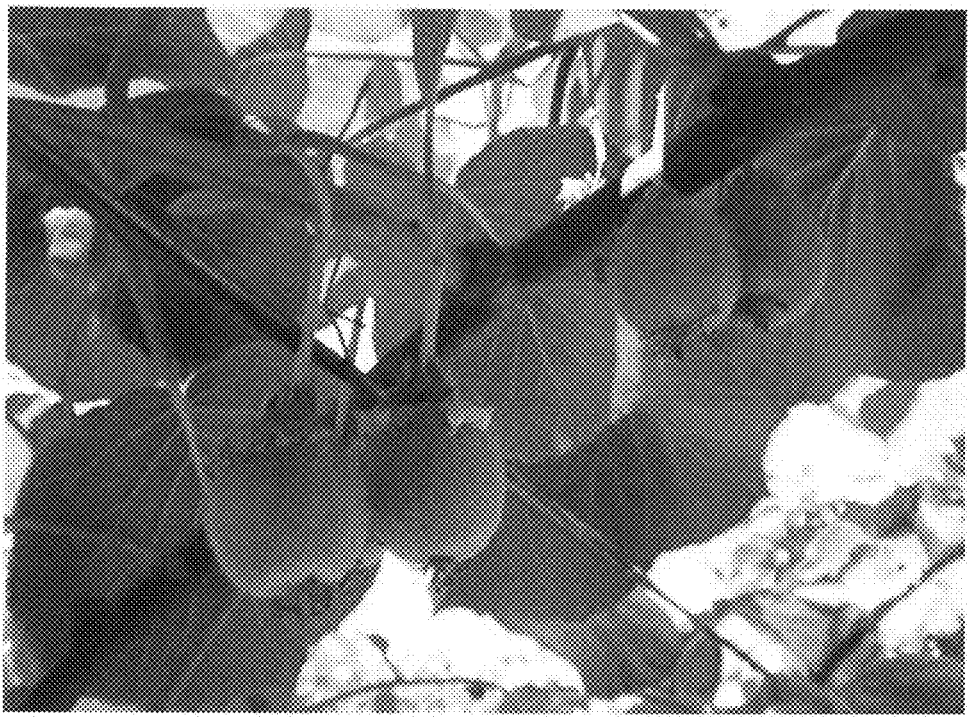
FIGS. 9-12 illustrate in full color typical foliage, hanging fruit, and stems on plants of 'AC1536'.
Figure 10:
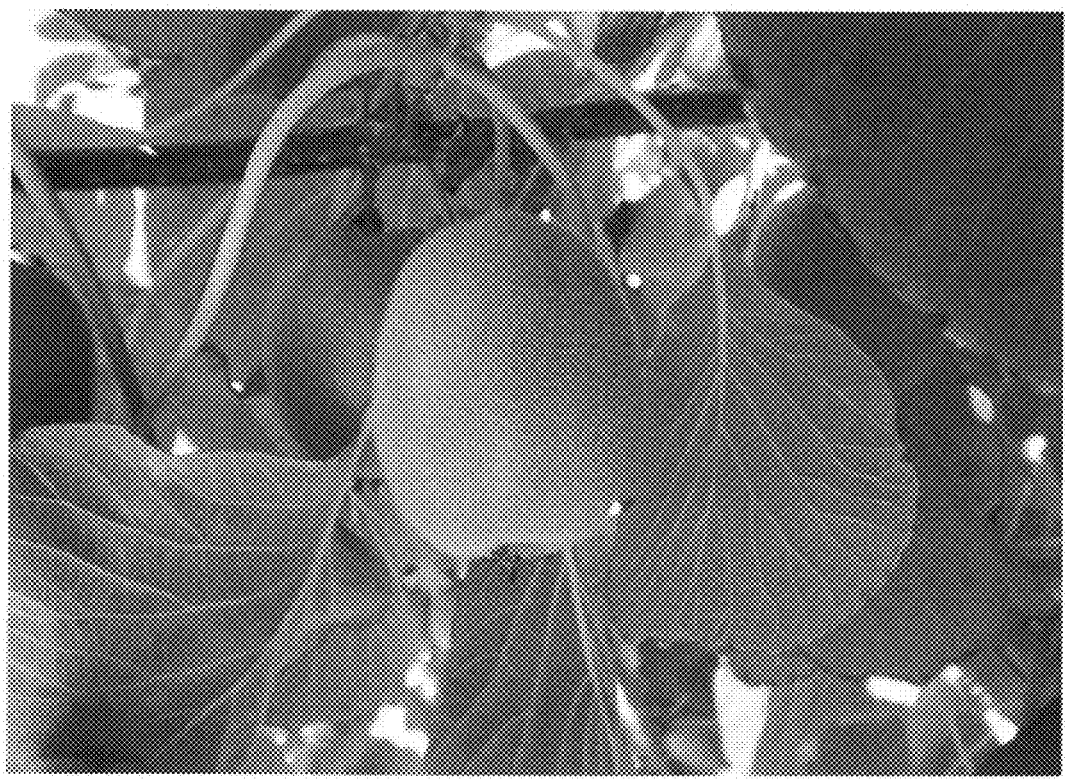
Figure 11:
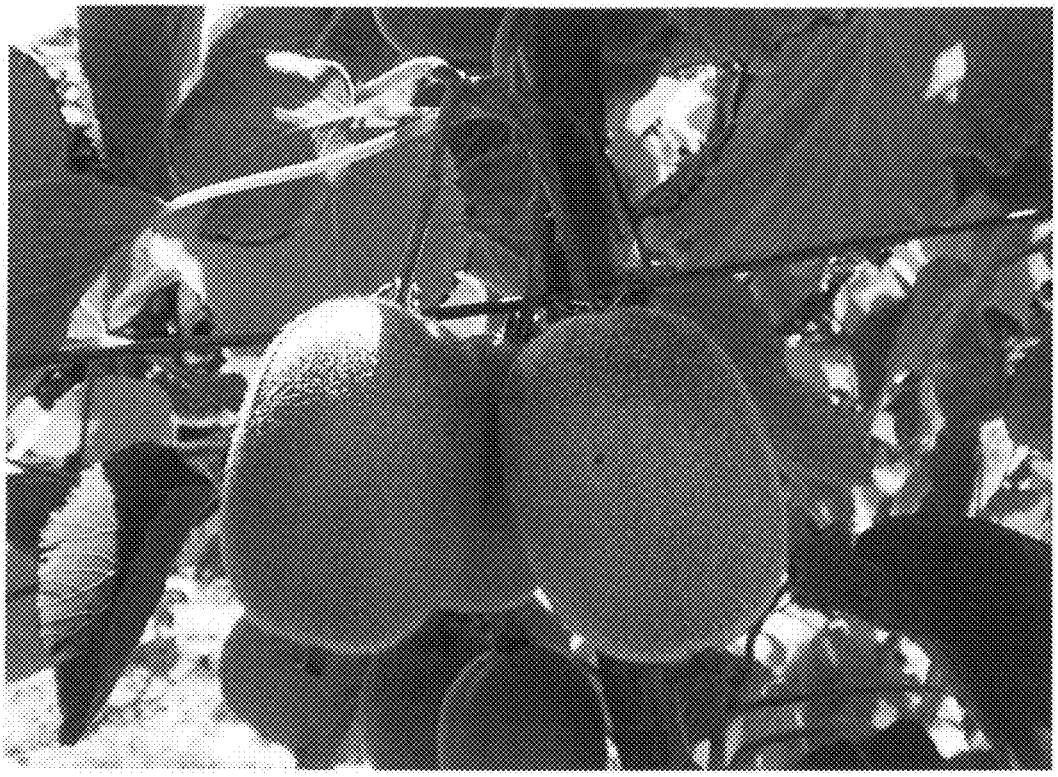
Figure 12:
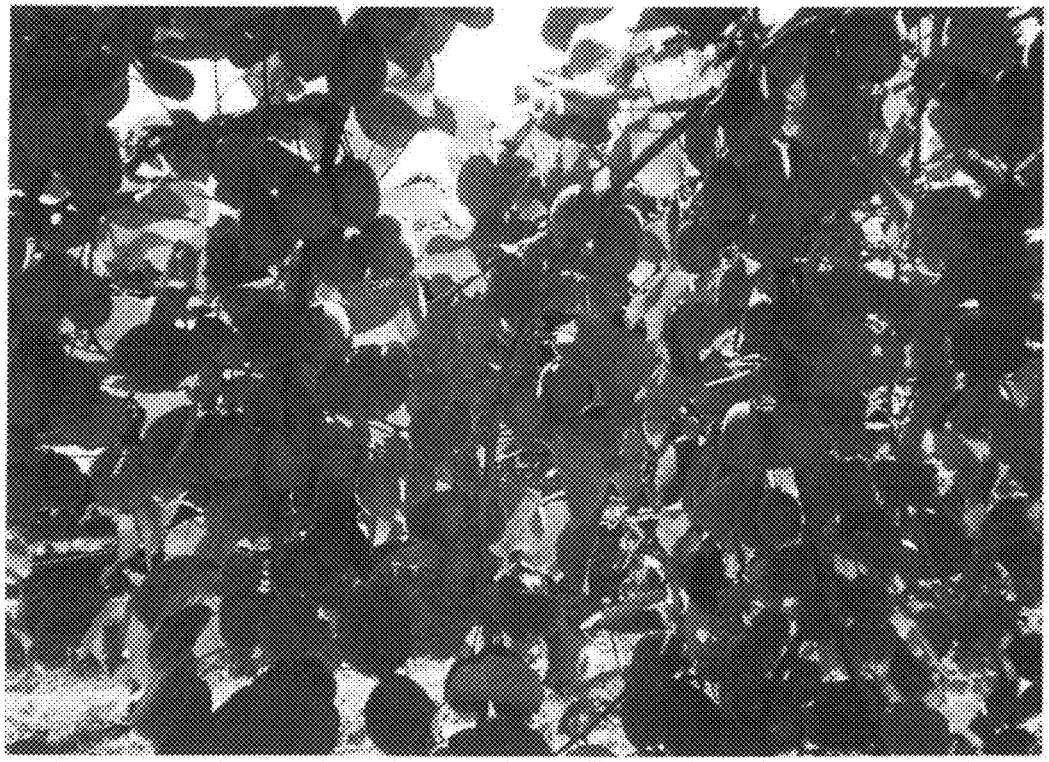
Figure 13:
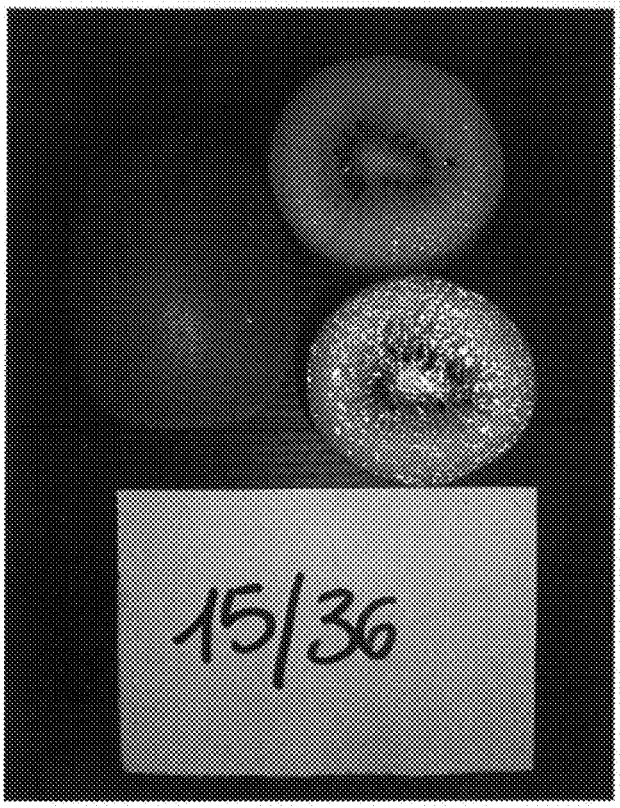
FIG. 13 illustrates in full color typical fruit harvested from 'AC1536'.
Figure 14:
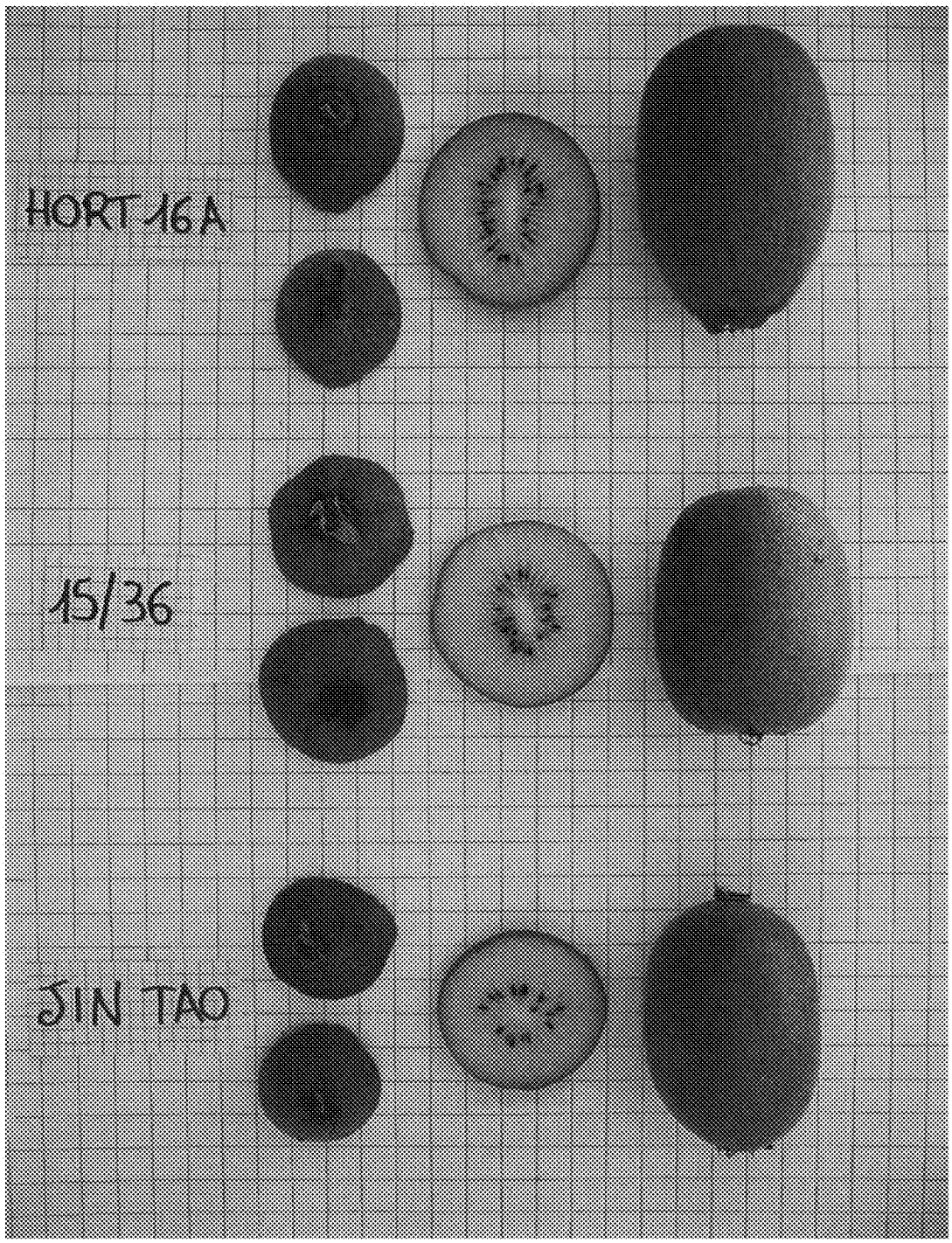
FIG. 14 illustrates in full color a side-by-side comparison of typical fruit harvested from 'AC1536' with typical fruit harvested from Hort16A and from Jintao.

All photographs are taken of plants that are approximately 4/5 years old. The photographs were taken using conventional techniques and although colors may appear different from actual colors due to light reflectance the colors are as accurate as possible by conventional photographic techniques.

DETAILED BOTANICAL DESCRIPTION

The following observations and measurements describe 'AC1536' plants grown outdoors under commercial trial conditions in Bologna, Italy. The growing temperature ranged from a minimum of −15° C. in winter (January) up to 40-42° C. in summer (July-August). The difference between daytime and nighttime temperatures during the summer is not extreme (usually less than 15° C.). Annual rainfall is approximately 600 mm per year. Measurements and numerical values represent an average of 10 typical plant types. Botanical classification: *Actinidia chinensis Planchon* 'AC1536'. Colors are referenced by The R.H.S. Dictionary of Color Propagation: 'AC1536' can be successfully grafted onto rootstocks of *Actnidia deliciosa* and *chinensis Planchon.*

Plant:

- *Age of the plant described.*—Approximately 10 years.
- *Sex expression.*—Female.
- *Ploidy.*—tetraDiploid.
- *Vigor.*—Weak-medium.
- *Young shoot color.*—Green.
- *Young shoot texture.*—Density of hair medium.
- *Cane diameter.*—Average approximately 1.5 cm.
- *Cane texture.*—Presence of hair.
- *Trunk texture and color.*—The trunk is intact and does not show evident cracking. Color Near RHS Grey-white 156C for 8-year-old plants, darkening as the plant ages.
- *Trunk diameter.*—Average approximately 7 cm in 10 years old plant.
- *Stem lenticels.*—Very small number and size of lenticels, irregularly spaced and sized. Oblong in shape, color grey-green.

Foliage:

- *Leaf.*—Length. — Approximately 2.2-14 cm; Average length. — Approximately 8 cm. Width. — Approximately 16-18.7 cm; Average width. — Approximately 17 cm.
- *Shape of blade.*—Very broadly obovate.
- *Apex.*—Acuminate.
- *Base.*—Cordate.
- *Attachment.*—Petioled.
- *Margin.*—Serrate, with few ciliate serrations.
- *Texture of top surface.*—Slightly puckered. Non-pubescent.
- *Texture of under side.*—Pubescent, slightly velveted.
- *Color.*—Near RHS Green N134C. Mature foliage under side: Near RHS Greyed-Green 192A.
- *Petiole.*—Length: Average length approximately 59 mm; Average diameter approximately 5 mm.
- *Pubescence.*—None.
- *Color.*—Upper surface red, lower surface orange-red.

Flower:

- *Flowers per inflorescence.*—Normally 1.
- *Bud color.*—Brown.
- *Bud shape.*—Typical for *Actinidia* (oblong).
- *Bud length.*—About 1 cm.
- *Bud diameter.*—About 6 mm.
- *Bud break.*—End of March.
- *First flower.*—Mid-May.
- *Diameter.*—Very large; average approximately 5.3 cm.
- *Typical and observed depth.*—About 5-10 mm.
- *Petal quantity.*—Average 6 per flower. Apex curvature: weakly expressed.
- *Petals overlapping.*—Yes.
- *Petals.*—Length — Average 31 mm. Width — Average 23 mm. Shape — Roundish. Margin — regular. Apex — none, roundish. Color. — Near RHS White 155A, with no significant differences between top and under surfaces.
- *Filament color.*—White.
- *Pedicle.*—Length — about 4 cm. Diameter — approximately 3 mm. Color — Near RHS Yellow-Green 145A.
- *Anther color.*—Yellow-orange.
- *Anther length.*—15-120 mm.
- *Attitude of styles.*—Semi-erect.
- *Style color.*—White.
- *Style quantity.*—Many more than 20.
- *Hair on ovary.*—Dense.
- *Ovary shape.*—Egg-shaped.
- *Color of ovary.*—White.
- *Number of sepals.*—Average 6.
- *Sepal shape.*—Regular.
- *Sepal apex.*—None.
- *Sepal margin.*—Regular acuminate, covered with fine tomentum.
- *Color of sepals.*—Near RHS Yellow-Green 145A with no significant differences between top and under surfaces.
- *Sepal width.*—Average approximately 0.7 cm.
- *Sepal length.*—Average approximately 0.9 cm.
- *Sepal texture.*—Smooth.
- *Peduncle.*—Length. — Average approximately 4 cm; Diameter: 4-5 mm. Color. — Yellow-green; Texture. — Smooth.
- *Chilling requirement.*—500-700 (about 600) hours.

Fruit:

- *Color outer pericarp.*—Near HHS Yellow 3C.
- *Color inner pericarp.*—Near RHS Yelow 3A or 6A.
- *Core color.*—Near RHS White 155A. The LCH colorimetric coordinates of a sample of the fruit are: L 71.4, C 39.9, H 96.76. The LAB colorimetric coordinates of a sample of the fruit are: L 71.4, A −4.7, B 39.6.

*Brix at consumption*.—Average approximately 16.0 degree Brix. — Average approximately 7.50 degree Brix at harvest in the beginning of September, up to average of approximately 16 degree Brix at 15 September. Average weight. — approximately 105 grams. Minimum weight. — approximately 90 grams. Maximum weight. — approximately 130 grams. Length. — Avg. approximately 7.2 cm. Width. — Avg. approximately 5.2 cm.

*Core diameter* (*maximum*).—Approximately 1.2 cm. Core diameter (minimum). — Approximately 0.7 cm.

*General shape*.—Oblong rectangular.

*Fruit peduncle length*.—Average approximately 5.0 cm.

*Fruit peduncle width*.—Average approximately 0.4 cm.

*General shape*.—Oblong.

*Shoulder shape*.—Squared.

*Calyx ring*.—Present. Calyx ring expression. — Weakly-expressed.

*Skin color at harvest*.—Yellow-brown.

*Hair on fruit skin*.—Downy.

*Hair adherence to skin*.—Moderate.

*Skin adherence to flesh at maturity*.—Moderate.

*Fruit core shape*.—Transversely elliptic.

*Core-woody spike*.—Absent.

*Lenticels on fruit*.—Minute, moderate in quantity, colored yellow-green.

*Mature seed color*.—Black.

*Dried seed*.—Brown. Usual harvest time $1^{st}$ decade ($1^{st}$-$10^{th}$) of September.

*Overall cropping quantity*.—30 to 50 tons per hectare.

*Locule number per fruit*.—From 33-44 locules in transverse section and an average of 300-400 seeds per fruit.

Other characteristics:

*Storage life*.—Storage life is a minimum of 3 months at 2 degrees C.

*Disease/pest resistance*.—Neither resistance nor susceptibility to pathogens and pests common to *Actinidia chinensis Planchon* have been observed.

*Temperature tolerance*.—Tolerates low temperatures to approximately −5 degrees C. and higher without negative effects, tolerates high temperatures to approximately 35 degrees C. without negative effects.

What is claimed is:

1. A new and distinct cultivar of the *Actinidia chinensis Planchon* plant named 'AC1536' as herein illustrated and described.

* * * * *